| United States Patent [19] | [11] Patent Number: 4,810,497 |
| Horrobin | [45] Date of Patent: Mar. 7, 1989 |

[54] PHARMACEUTICAL COMPOSITIONS

[75] Inventor: David F. Horrobin, Haslemere, United Kingdom

[73] Assignee: Efamol Limited, London, England

[21] Appl. No.: 147,208

[22] Filed: Jan. 22, 1988

Related U.S. Application Data

[62] Division of Ser. No. 7,109, Jun. 27, 1987, Pat. No. 4,753,964.

[30] Foreign Application Priority Data

Jan. 27, 1986 [GB] United Kingdom ................. 8601915

[51] Int. Cl.$^4$ ..................... A61K 31/20; A61K 31/61; A61K 31/195; A61K 31/615; A61K 33/04; A61K 33/14
[52] U.S. Cl. .................................... 424/153; 424/163; 514/162; 514/558; 514/500; 514/561
[58] Field of Search ............... 514/558, 560, 162, 163, 514/561; 424/153

Primary Examiner—Stanley J. Friedman
Attorney, Agent, or Firm—Foley & Lardner, Schwartz, Jeffery, Schwaab, Mack, Blumenthal & Evans

[57] ABSTRACT

Presenile and senile dementia, in particular Alzheimer's disease, can be combated or alleviated by administration of an effective amount of a physiologically acceptable lithium compound and an essential fatty acid or a physiologically acceptable salt thereof.

15 Claims, No Drawings

PHARMACEUTICAL COMPOSITIONS

This application is a division, of application Ser. No. 007,109, filed Jan. 27, 1987, now U.S. Pat. No. 4,153,964.

This invention relates to a method of treatment of presenile and senile dementia, including in particular Alzheimer's disease, as well as to the use of substances for the manufacture of therapeutic agents for use in such treatment and to pharmaceutical compositions for use in such treatment.

Dementia and especially Alzheimer's disease may involve progressive deterioration of brain function resulting in a loss of the individual's ability to lead a normal life. It may occur prematurely in the subject's 50's or earlier and may appear as an unusually severe acceleration of normal ageing.

At present the cause of Alzheimer's disease is unknown and there is no certain treatment.

Our investigations suggest that dementias such as Alzheimer's disease are related to an imbalance in the conversion of essential fatty acids (EFAs) to prostaglandins (PGs). In normal ageing, red cell membrane fluidity decreases (i.e. the membrane becomes stiffer) and the production of cyclic adenosine monophosphate (AMP) by cells such as lymphocytes declines. The changes in Alzheimers' disease are diametrically opposite, with an unexpected increase in cell membrane fluidity and a rise in cyclic AMP levels occurring. Certain PGs, such as $PGE_1$ (formed from dihomogammalinolenic acid (DGLA)), $PGI_2$ (formed from arachidonic acid (AA)) and $PGI_3$ (formed from eicosapentaenoic acid (EPA)) are known to be able to increase membrane fluidity and cyclic AMP levels. Thus we believe that the unexpected changes in Alzheimer's disease could be explained as arising from excessive conversion of EFAs to PGs. The EFAs are essential components of the structure of all cell membranes in the body, particularly of those in the brain in which EFA levels are exceptionally high. An uncontrolled and excessive conversion of EFAs from the cell membranes, where they are primarily found in the phospholipid form, into PGs would be expected to lead to structural damage to and functional impairment of cell membrane function. This is however only offered as a possible theoretical explanation and the utility of the present invention is not of course dependant on this explanation being correct.

It is an object of the present invention to provide a method or a therapeutic agent for treating subjects to combat dementias such as Alzheimer's disease.

In one aspect the invention provides a method of treating a warm blooded animal subject, to combat or to alleviate effects of presenile or senile dementia, in particular Alzheimer's disease, which method comprises administering to said subject an effective amount of a physiologically acceptable lithium compound.

Lithium compounds are used according to the method of the present invention in view of their ability to reduce production of cyclic AMP and to inhibit the metabolic conversion of EFAs to PGs, in part by inhibiting the metabolism of phosphatidylinositol. Administration of lithium may therefore serve to correct any imbalance in the conversion of EFAs to PGs and thus be of benefit in the treatment of dementia and in particular of Alzheimer's disease.

The administration of the lithium compound according to the invention is conveniently parenteral or, preferably, oral and the compound, which is in a form from which lithium ions are biologically accessible, is preferably a salt such as the carbonate, citrate, succinate, chloride, bromide, acetate, acetylsalicylate, benzoate, bitartrate, nitrate, selenate, selenite, sulphate, aspartate, gluconate or thenoate.

The daily dosage of the lithium compound for the adult human will generally be in the range of 1 to 2000 mg, preferably 20–600 mg, especially 50–600 mg of lithium ion although precise dosages will depend upon factors such as the patient's body weight and the severity of the condition. The lithium plasma level will generally be monitored and the rate of administration adjusted to provide a suitable concentration in the plasma, e.g. of 0.05 to 1.6 mM lithium per liter.

Besides acting as PG bioprecursors, the EFAs are themselves important in the body chemistry and EFA depletion may be responsible for certain effects of dementias such as Alzheimer's disease. Thus in a preferred embodiment of the invention EFAs are also administered to the subject, again conveniently orally or parenterally, if desired simultaneously with the lithium compound. Indeed, in view of the risks of EFA depletion, the EFAS may be administered to patients suffering from Alzheimer's disease even in the absence of lithium treatment. Thus in a further aspect the invention provides a method of treating a warm blooded animal subject, in particular a human, to combat or to alleviate effects of presenile or senile dementia, in particular Alzheimer's disease, which method comprises administering to said subject an effective amount of an essential fatty acid, or a physiologically acceptable salt thereof, optionally in conjunction with the administration to said subject of a physiologically acceptable lithium compound.

The term "essential fatty acids" is used herein in its conventional sense to refer to the two fatty acid series comprising linoleic acid (LA), gamma-linolenic acid (GLA), dihomogammalinolenic acid (DGLA), arachidonic acid (AA), adrenic acid and 22:5n-6 and alpha-linolenic acid (ALA), 18:4n-3, 20:4n-3, eicosapentaenoic acid (EPA), 22:5n-3 and docosahexaenoic acid (DHA).

Particularly preferred EFAs for administration according to the invention are DGLA, AA, EPA, DHA, LA, GLA, ALA and 18:4n-3. For the purposes of the present invention, a particularly suitable source of GLA and LA is found in evening primrose oil. Where the EFA is administered in the form of a salt thereof, it is particularly preferred to employ the lithium salt as one salt will thus provide both active ingredients. Daily dosages of the EFAs will again be dependent on factors such as body weight and the severity of the condition but will generally be in the range 1 mg to 200 g for the adult human. For LA and ALA, daily dosages are preferably 100 mg to 200 g, especially preferably 2–30 g, while for other fatty acids such as GLA, DGLA, AA, 18:4n-3, EPA and DHA daily dosages will preferably be 1 mg to 50 g, especially preferably 20 mg to 10 g.

In a further aspect, the invention provides the use of a physiologically acceptable lithium compound for the manufacture of a therapeutic agent for combatting presenile or senile dementia, in particular Alzheimer's disease.

In a still further aspect, the invention provides the use of an essential fatty acid or a physiologically acceptable salt thereof, optionally together with a physiologically acceptable lithium compound, for the manufacture of a therapeutic agent for combatting presenile or senile dementia, in particular Alzheimer's disease.

In a yet still further aspect, the invention provides a pharmaceutical composition for combatting presenile or senile dementia, in particular Alzheimer's disease and comprising as active ingredient a physiologically acceptable lithium compound and/or an essential fatty acid or a physiologically acceptable salt thereof, conveniently together with at least one pharmaceutical carrier or excipient.

The pharmaceutical compositions of or manufactured according to the present invention are preferably in dosage unit form, e.g. in the form of tablets, coated tablets, capsules etc, advantageously containing 100 to 1200 mg of the lithium compound and/or 50 to 1200 mg of EFA or salts thereof.

The following non-limiting Examples serve to illustrate compositions which may be used in the methods of the invention:

EXAMPLE 1

TABLETS

Tablets are prepared by conventional methods using conventional tabletting aids and the following lithium salts:

| Tablet No. | Lithium Salt | Wt. of Lithium salt per tablet |
|---|---|---|
| 1 | Carbonate | 300 mg |
| 2 | Succinate | 400 mg |
| 3 | Citrate | 400 mg |
| 4 | Sulphate | 250 mg |

EXAMPLE 2

Capsules

Capsules are prepared by coventional methods using conventional aids, (e.g. gelatin cases) and with the following active ingredients per capsule:

| Capsule No. | Lithium Salt | EFA | |
|---|---|---|---|
| 1 | — | Evening primrose oil* | (500 mg) |
| 2 | — | DGLA | (50 mg) |
|   |   | AA | (50 mg) |
|   |   | EPA | (50 mg) |
|   |   | DHA | (50 mg) |
| 3 | Succinate (200 mg) | GLA | (45 mg) |
|   |   | LA | (360 mg) |
| 4 | Carbonate (250 mg) | GLA | (50 mg) |
|   |   | LA | (200 mg) |
|   |   | ALA | (10 mg) |
|   |   | 18:4n-3 | (20 mg) |
| 5 | Citrate (200 mg) | EPA | (25 mg) |
|   |   | DHA | (30 mg) |
|   |   | GLA | (40 mg) |
| 6 | Lithium Gammalinolenate (1000 mg) | | |
| 7 | Lithium Gammalinolenate (500 mg) Lithium Eicosapentaenoate (500 mg) | | |

*containing GLA (45 mg) and LA (360 mg)

I claim:

1. A method of treating a warm blooded animal subject to combat or to alleviate effects of presenile or senile dementia, which method comprises administering to said subject an effective amount of a physiologically acceptable lithium compound, such that said lithium compound is administered at a rate of about 1 mg to about 2000 mg of lithium ions daily, and a fatty acid compound selected from the group consisting of an essential fatty acid and a physiologically acceptable salt thereof, wherein said fatty acid compound is administered at a rate of about 1 mg to about 200 g daily.

2. A method as claimed in claim 1, wherein said amount is effective in combating or alleviating effects of Alzheimer's disease.

3. A method as claimed in claim 2, wherein said lithium compound is a lithium salt.

4. A method as claimed in claim 2, wherein said lithium compound is selected from the group consisting of lithium carbonate, lithium citrate, lithium succinate, lithium chloride, lithium bromide, lithium acetate, lithium acetylsalicylate, lithium benzoate, lithium bitartrate, lithium nitrate, lithium selenate, lithium selenite, lithium sulphate, lithium aspartate, lithium gluconate and lithium thenoate.

5. A method as claimed in claim 2, wherein said lithium compound is administered in a quantity sufficient to provide a plasma lithium level of 0.05 to 1.6 mM lithium/liter.

6. A method as claimed in claim 1, wherein said fatty acid compound is selected from the group consisting of dihomogammalinolenic acid, arachidonic acid, docosahexaenoic acid, linolenic acid, gamma-linolenic acid, alphalinolenic acid, 18:4n-3 and physiologically acceptable salts of any of the foregoing essential fatty acids.

7. A method as claimed in claim 1 comprising administering to said subject a lithium salt of an essential fatty acid.

8. A method as claimed in claim 1, wherein said administration is carried out orally or parenterally.

9. A method as claimed in claim 8, wherein said lithium compound is administered orally in the form of a liquid, a tablet, a capsule or a sachet.

10. A method as claimed in claim 1, wherein said lithium compound is administered at a rate of about 20 mg to 600 mg of lithium ions daily.

11. A method as claimed in claim 1, wherein said lithium compound is administered at a rate of about 50 g to 600 mg of lithium ions daily.

12. A method as claimed in claim 6, wherein said fatty acid compound is selected from linolenic and alphalinolenic acid, and is administered at a rate of about 100 mg to about 200 g daily.

13. A method as claimed in claim 12, wherein said fatty acid compound in administered at a rate of about 2 g to about 30 g daily.

14. A method as claimed in claim 6, wherein said fatty acid compound is selected from gamma-linolenic acid, dihomogammalinolenic acid, arachidonic acid, 18:4n-3, eicosapentaenoic acid and docosahexaenoic acid, and is administered at a rate of about 1 mg to about 50 g daily.

15. A method as claimed in claim 14, wherein said fatty acid compound is administered at a rate of about 20 mg to 10 g daily.

* * * * *